United States Patent [19]
Hoshino et al.

[11] 4,195,130
[45] Mar. 25, 1980

[54] PROPAGATION OF FELINE INFECTIOUS PERITONITIS VIRUS IN TISSUE CULTURES

[75] Inventors: Yasutaka Hoshino; Fredric W. Scott, Brooktondale, both of N.Y.

[73] Assignee: Cornell Research Foundation, Inc., Ithaca, N.Y.

[21] Appl. No.: 898,057

[22] Filed: Apr. 20, 1978

[51] Int. Cl.² .............................................. C12N 7/00
[52] U.S. Cl. ...................................................... 435/235
[58] Field of Search ........................................ 195/1.1

[56] References Cited
PUBLICATIONS

Pedersen—(abstract 6514), The Veterinary Bulletin, vol. 46, No. 7 (Jul., 1976), p. 857.

Ward et al.—Am. J. of Vet. Research, vol. 35 No. 10, Oct., 1974, pp. 1271-1275.

Pedersen—Am. J. of Vet. Research, vol. 37, No. 5, May, 1976, pp. 567-572.

*Primary Examiner*—Sam Rosen
*Attorney, Agent, or Firm*—Jones, Tullar & Cooper

[57] ABSTRACT

This invention relates to a method for the propagation of feline infectious peritonits (FIP) virus by means of tissue culture. It has been found that FIP virus can be propagated in organ cultures, for example, using feline tracheal rings or small intestine, as well as monolayer cell cultures, for example, using feline kidney, lung or embryo cell cultures.

10 Claims, 6 Drawing Figures

PROPAGATION OF FELINE INFECTIOUS PERITONITIS VIRUS IN TISSUE CULTURES

BACKGROUND OF THE INVENTION

As discussed by Pedersen, *Feline Practice* May 1977, 13–14, feline infectious peritonitis (FIP) virus infection is very widespread in cats, with approximately 25% of normal urban cats having experienced the infection. The infection rate is even higher in catteries and multiple cat households, approaching 100% in many. These asympotmatic cats have antibody titers, with some apparently being immune to the disease, while others are apparently chronic carriers of the disease.

It is theorized that following infection with FIP virus, cats undergo some sort of primary illness, usually a mild respiratory disease which has not yet been defined fully. Following this primary infection most cats apparently recover. A proportion of these cats, however, will become chronically infected. Some of these chronically infected cats will remain asymptomatic, while others will develop serositis or granulomatous disease (effusive or non-effusive FIP) over a period of time. (See also Pedersen *Feline Practice* May 1976, 42–51).

Recently a new test for antibodies to FIP virus (Pedersen, *Amer. J. Vet. Res.*, 37, 1449–1453, 1976) makes possible a more effective study of the epidemiology and pathogenesis of the disease.

One major drawback in the study of FIP virus has been the failure to find a method adapted to large-scale in vitro cultivation of the FIP virus. Large-scale in vitro production of the virus is useful in studying the virus, its structure, antibody and drug responses, and as well as the epidemiology and pathogenesis of the disease. Also such in vitro virus production would make possible the economical production of a virus based FIP vaccine.

Heretofore, attempts to replicate FIP virus in vitro have been unsuccessful. Pedersen, *Amer. J. Vet. Res.*, 37, 567–571, 1976, has described the replication of FIP virus in autochthonous peritoneal cell cultures, but acknowledges that this technique falls short of a reasonable virus production method. (See also Ward et al, *Amer. J. Vet. Res.*, 35, 1271–1275, 1975).

FIP virus has been characterized as being a virus similar in size morphology and budding characteristics to members of the coronavirus group. (Pedersen, *Amer. J. Vet. Res.*, 37, 1449–1453, 1976; Starks et al *Amer. J. Vet. Res.*, 37, 335–338, 1976.)

Cook et al, *Archives of Virology*, 50, 109–118 (1976) describe the use of chicken trachial organ cultures for the replication of avian infectious bronchitis virus.

Stott et al, *Veterinary Microbiology*, 1, 65–69 (1976) describe the replication of a bovine coronavirus in organ cultures of fetal trachea.

Cook et al, *Research in Vet. Sci.*, 20, 348–349 (1976) describe the propagation of several strains of avian infectious bronchitis virus in trachial organ cultures.

DESCRIPTION OF THE INVENTION

Figure 1A:
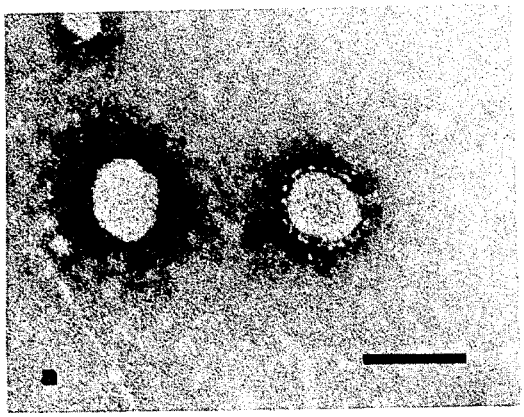
FIGS. 1 a through f are electron micrographs of negatively stained FIP virus particles from small intestine organ culture fluid (Example II) 1–43 days after inoculation of cultures with a 10% suspension of liver from FIP infected cats. The bar represents 100 nm.

This invention relates to a method for the propagation of feline infectious peritonitis virus by means of tissue cultures. It has been discovered that FIP virus can be propagated in tissue cultures of feline trachea and small intestine, and in monolayer cultures of feline cells, such as kidney, lung and embryo.

In the process of the invention feline trachea tissue cultures are inoculated with FIP virus and maintained in a culture media at a virus propagation promoting temperature below normal feline body temperature preferably between about 30° C. and about 36° C. and most preferably at a temperature between about 32° C. and about 34° C.

In the examples of this invention tissue origin FIP viruses from two different sources were used. One strain (tenatively P. strain) passed in kittens was obtained as a 50% liver suspension from Dr. N. C. Pedersen, University of California, who has described the morphology and physical characteristic of FIP virus in *Amer. J. Vet. Res.*, 37, 567–572 (1976). This virus was passed twice in kittens after its receipt, and stored as a 50% suspension of liver tissue. Another strain (tenatively G. strain) was obtained from Dr. Gaskin, University of Florida, Gainsville, and was a 33% suspension of omentum from a classic case of wet FIP.

EXAMPLE I

The tracheas for tracheal organ cultures were obtained from 2-day-old to 9-week-old SPF kittens. The trachea from the larynx to the thoracia inlet was removed as soon as possible after death, and submerged in PBS pH 7.4, supplimented with 100 units ml of penicillin and 100 μg/ml streptomycin and all further preparation was carried out in this medium.

Excess tissue was carefully removed from the outside of the trachea and vigorously pipetted with medium to remove any mucous from the epithetial surface. The 0.5 mm to 1 mm transverse ring sections were cut with a scalpel; each trachea yielding about 16 to 30 rings.

Each ring was placed in a standard rubber stoppered tissue culture tube (16×125 mm) to which was added 1 ml of a standard cell culture medium, for example, McCoy 5a medium (GIBCO) with 0.4% bovine serum albumin, 5% tryptose phosphate broth, 100 units/ml penicillin and 100 μg/ml streptomycin. The tubes were placed in a roller drum (15 rev/hr) and incubated at 33° C. with the medium being changed at 1 to 2 week intervals. Ciliary activity, an indication of the viability of the organ culture, persisted for at least two months.

Each tissue culture was inoculated with 0.2 ml of FIP virus (1:5 dilution of 50% feline liver suspension in PBS). Absorption was carried out at 37° C. for one hour. After absorption, excess inoculum was removed and the organ ring vigorously washed three times, each time with 1 ml each of PBS pH 7.4, to remove unabsorbed virus. One ml of the culture medium described above was added to each tube and the tube incubated in a roller drum at 33° C.

No ciliastasis of the trachea organ culture was observed, although many viruses are capable of replication in organ cultures with few or no histological evidence of infection. Multiplication of some viruses in ciliated epithelium does not always affect ciliary activity.

Figure 1B:
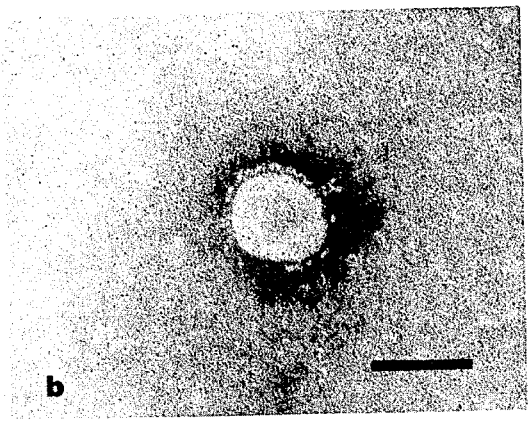
Figure 1C:
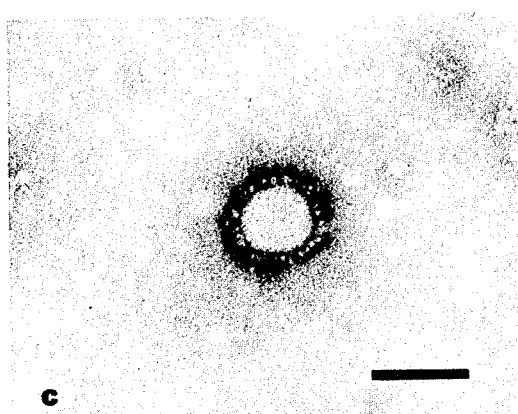
Figure 1D:
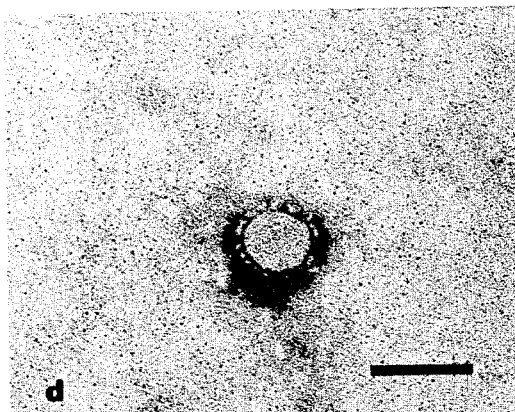
Figure 1E:
Figure 1F:
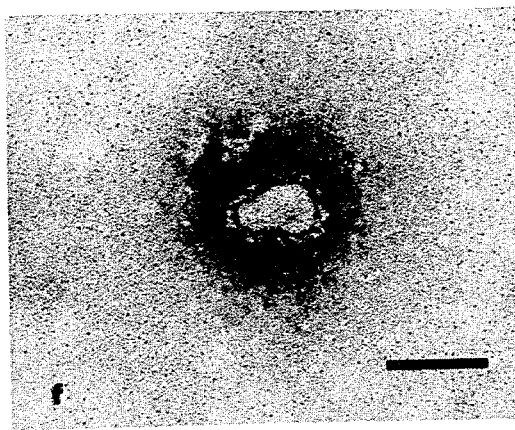

After 4, 5, 8, 17 and 35 days four ml of infected organ culture fluid was clarified by centrifugation at 6,000 rpm for 30 minutes. The supernatant fluid was then centrifuged at 39,000 rpm for 60 minutes. The pellet of material was resuspended in one drop of distilled water and a drop placed on an electron microscope grid, stained with 2% phosphotungstic acid, pH 6.5 and examined in a Philips 201 electron microscope at 80 KV. In each instance the electron microscope revealed particles with characteristic coronavirus morphology. Pleomorphism occurred in the virions seen in the tracheal culture fluids, although the majority of the particles ranged in size, inclusive of projections, from 90 to 150 nm. The virions had radiating projections (approximately 15 nm in length) giving the characteristic appearance of coronaviruses (FIG. 1). The virions also show the consistent appearance of the central electron-dense area reported with other coronaviruses.

Electronmicroscopic examination of culture fluid from uninoculated organ culture was negative for virions.

EXAMPLE II

Feline intestinal organ cultures were prepared from the small-intestine of 1-day to 9-week old SPF kittens.

The intestine was aseptically removed from the kittens, placed in PBS pH 7.4 with 250 units/ml penicillin and 250 μg/ml streptomycin, and vigorously pipetted with medium to remove meconium, intestinal contents and other debris. 2 to 3 mm transverse ring sections were cut with a scalpel and were placed individually in 16×125 mm tubes. One ml of a standard maintainence culture medium, for example, Leibovitz L-15 medium (GIBCO) supplemented with 0.5% bovine serum albumin, 5% tryptose phosphate broth, 250 units/ml penicillin, 250 μg/ml streptomycin and 2.0 nM glutamine, was added, and the tubes placed in a roller drum (15 rev/hr) and incubated at 33° C.

Individual tissue cultures were inoculated with FIP virus, as in Example I, but using the culture medium described above. The tubes were then incubated in a roller drum at 33° C.

After 1, 2, 5, 11, 15, 22, 31 and 33 days the infected organ culture fluid was worked up and examined by electron microscopy as in Example 1. In each case virions identical to those described in Example 1 were observed. FIGS. 1 a-f are electron micrographs of the virus particles observed.

Examination of uninoculated organ culture controls by electron microscopy was negative for virions.

EXAMPLE III

Tissue rings from both in virus inoculated tracheal and small intestine organ cultures were frozen in liquid nitrogen and sectioned in a cryostat. Sections were maintained on glass slides, fixed in cold acetone (−20° C.), and tested for the presence of FIP antigen by the indirect fluorescent antibody test following the technique of Pedersen, *Amer. J. Vet. Res.*, 37, 1448-1453 (1976).

Known FIP positive and negative sera were applied to respective sections, incubated at room temperature in a moisture chamber, and rinsed with water; then a FITC-conjugated rabbit anti-cat IgG serum was applied to all sections. After inoculation as above, the sections were rinsed with water, dried, and examined for specific fluorescence using an ultraviolet microscope.

Sections from FIP virus inoculated cultures treated with the FIP positive serum had specific fluorescence in the cytoplasm of cells. Negative serum treated sections and all sections from uninoculated controls did not have fluorescence.

EXAMPLE IV

Monolayer cultures of feline kidney, feline lung (first transfered), and a cell line of feline embryo cells were seeded on plastic culture flasks and Leighton tube cover slip cultures, and incubated at 33° C. Twenty-four hours after seeding, the cultures were inoculated with fluid from the feline intestine organ cultures of Example II. Cultures were examined daily for CPE, and at varying intervals from 3 to 7 days after inoculation, cultures were harvested and passaged in the same type of culture for up to a total of 5 passages. At varying intervals cultures were examined for the presence of FIP virus by the indirect immunofluorescence test (Example III) and by electron microscopy (Examples I and II). By both tests inoculated cultures were determined to contain FIP virus.

Using the appropriate temperature, as above, and other appropriate environmental conditions it is believed that FIP virions can be propagated in feline tissue cultures of other tissues or other feline cell lines such as Crandell Feline Kidney (CrFK), feline Neurofibrosarcoma cell line (FNFS), Feline tongue cell line.

A transmission experiment in 6-month-old SPF cats was performed with infected small intestine organ culture fluid (Example II). Two experimental cats and an age-matched contact control cat were housed together in standard Horsfall isolation cage. A negative control cat was caged separately. Two cats were inoculated with a total of 20 ml each of pooled infected culture fluid (10 ml on day 0 and 10 ml on day 1, intraperitoneally). The negative control cat received the same amount of uninfected control culture fluid. Cats were observed daily for signs of illness, and serum samples were collected weekly for serum antibody assay. One of two cats inoculated with infected fluid was first observed ill on day 33 and died on day 37 postinfection. Clinically, signs of anorexia, dehydration, listlessness, weight loss, and abdominal enlargement were present. Necropsy examination revealed this was classical effusive form of FIP: an extensive accumulation of abdominal fluid with fibrin flakes, small white foci of necrosis in the liver, thickened omentum of gelatinous consistency, and deposits of granular, grey-white exudate intermittently present on serosa of the abdominal viscera. There was no excess of pleural fluid.

To detect seroconversion to FIP virus, the indirect fluorescent antibody (IFA) test was performed following the technique of Pedersen (supra). The IFA titers of both serum and peritoneal fluid of the cat showing signs of FIP taken at necropsy on day 37 were >1:1,600. The second infected cat showed no clinical symptoms but seroconverted with an IFA titer of 1:400 on day 35. Both negative and contact controls remained serologically negative.

Table 1 shows IFA test results of the serum samples of infected, negative control, and contact control cats.

TABLE 1

Serum Antibody Titers Against FIP Virus of Infected, Negative Controls, and Contact Control Cats.

| Post Exposure Day | IFA Serum Antibody Titer Against FIP Virus | | | |
|---|---|---|---|---|
| | Infected | | Negative Control | Contact Control |
| | Cat A | Cat B | | |
| 0 | <1:25 | <1:25 | <1:25 | <1:25 |
| 7 | <1:25 | <1:25 | <1:25 | <1:25 |
| 14 | <1:25 | <1:25 | <1:25 | <1:25 |
| 21 | <1:25 | <1:25 | <1:25 | <1:25 |

TABLE 1-continued

Serum Antibody Titers Against FIP Virus of Infected, Negative Controls, and Contact Control Cats.

| Post Exposure Day | IFA Serum Antibody Titer Against FIP Virus: Infected Cat A | Infected Cat B | Negative Control | Contact Control |
|---|---|---|---|---|
| 28 | NT | NT | NT | NT |
| 33 | >1:1,600 | NT | NT | NT |
| 35 | >1:1,600 | 1:400 | <1:25 | <1:25 |
| 37 | >1:1:600* | NT | NT | NT |
| 42 | — | 1:400 | <1:25 | <1:25 |

*IFA titers of both serum and peritoneal fluid taken at necropsy.
NT = not tested The tissue culture technique of the invention provides a method to further the study of pathogenesis, epidemiology, and eventually the prevention of FIP.

While these have been described above, the invention and what presently are believed to be its best embodiments, it is understood that the invention can be practicied otherwise within the scope of the following claims.

We claim:

1. A method of propagating feline infectious peritonitis virus which comprises culturing the virus in a feline infectious peritonitis virus growth supporting feline tissue culture at a feline infectious peritonitis virus propagation promoting temperature below normal feline body temperature.

2. A method as in claim 1 where the virus is cultured at a temperature between about 30° C. and about 36° C.

3. A method as in claim 1 where the virus is cultured at a temperature between about 32° C. and about 34° C.

4. A method as in claim 1 where the tissue comprises feline tracheal rings.

5. A method as in claim 1 where the tissue comprises feline small intestinal rings.

6. A method as in claims 1, 2, or 3 where the tissue culture comprises feline tracheal rings, feline small intestinal rings, feline kidney cells, feline lung cells or feline embryo cells.

7. A method of propagating feline infectious peritonitis virus which comprises culturing the virus in a feline infectious peritonitis virus growth supporting feline tissue culture comprising feline traceal tissue, feline small intestinal tissue, feline kidney cells, feline lung cells or feline embryo cells at a feline infectious peritonitis virus propagation promoting temperature below normal feline body temperature.

8. A method as in claim 7 where the virus is cultured at a temperature between about 30° C. and about 36° C.

9. A method of propagating feline infectious peritonitis virus which comprises inoculating the virus into and culturing the virus in a feline infectious peritonitis virus growth supporting feline tissue culture at a feline infectious peritonitis virus propagation promoting temperature below normal feline body temperature.

10. A method of propagating feline infectious peritonitis virus which comprises inoculating the virus into and culturing the virus in a feline infectious peritonitis virus growth supporting feline tissue culture comprising feline traceal tissue, feline small intestinal tissue, feline kidney cells, feline lung cells or feline embryo cells at a feline infectious peritonitis virus propagation promoting temperature below normal feline body temperature.

* * * * *